(12) United States Patent
Powers

(10) Patent No.: US 9,669,229 B2
(45) Date of Patent: *Jun. 6, 2017

(54) AUTOMATIC EXTERNAL DEFIBRILLATOR FOR ADULT AND PEDIATRIC PATIENTS

(71) Applicant: KONINKLIJKE PHILIPS N.V., Eindhoven (NL)

(72) Inventor: Daniel J. Powers, Issaquah, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/730,374

(22) Filed: Jun. 4, 2015

(65) Prior Publication Data

US 2015/0273224 A1    Oct. 1, 2015

Related U.S. Application Data

(63) Continuation of application No. 11/721,549, filed as application No. PCT/IB2005/054249 on Dec. 14, 2005, now Pat. No. 9,079,044.

(60) Provisional application No. 60/637,682, filed on Dec. 20, 2004.

(51) Int. Cl.
*A61N 1/39*    (2006.01)

(52) U.S. Cl.
CPC ......... *A61N 1/3925* (2013.01); *A61N 1/3912* (2013.01); *A61N 1/3968* (2013.01); *A61N 1/3993* (2013.01)

(58) Field of Classification Search
CPC ........................... A61N 1/3925; A61N 1/3968
See application file for complete search history.

(56) References Cited

U.S. PATENT DOCUMENTS

| | | | |
|---|---|---|---|
| 5,607,454 A | 3/1997 | Cameron et al. | |
| 5,735,879 A | 4/1998 | Gliner et al. | |
| 5,836,993 A | 11/1998 | Cole | |
| 5,879,374 A | 3/1999 | Powers et al. | |
| 6,125,298 A * | 9/2000 | Olson | A61N 1/39 607/5 |
| 6,134,468 A | 10/2000 | Morgan et al. | |
| 6,356,785 B1 | 3/2002 | Snyder et al. | |
| 6,370,428 B1 | 4/2002 | Snyder et al. | |
| 6,374,137 B1 | 4/2002 | Morgan et al. | |
| 6,556,864 B1 * | 4/2003 | Picardo | A61N 1/39 607/5 |
| 9,079,044 B2 * | 7/2015 | Powers | A61N 1/3925 |
| 2003/0055459 A1 * | 3/2003 | Lyster | A61N 1/046 607/5 |

(Continued)

FOREIGN PATENT DOCUMENTS

| | | |
|---|---|---|
| EP | 0801959 A | 10/1997 |
| JP | H034467 | 1/1991 |

(Continued)

*Primary Examiner* — Eric D. Bertram

(57) ABSTRACT

An AED unit is operable to selectively switch to a pediatric rescue protocol by inserting a key-like device into an aperture of the AED unit. A sensor inside the case of the AED unit senses the presence of the device in the slot and responds by executing the pediatric rescue protocol. A separate electrode pad mating connector on the AED unit receives an electrode pad connector, the associated electrode pads being suitable for either adult or pediatric patients.

20 Claims, 5 Drawing Sheets

(56) References Cited

U.S. PATENT DOCUMENTS

2003/0171798 A1* 9/2003 Nova ................... A61N 1/04
607/142
2003/0216785 A1 11/2003 Edwards et al.
2004/0249419 A1* 12/2004 Chapman ............ A61N 1/3925
607/5

FOREIGN PATENT DOCUMENTS

| JP | 2002246107 A | 8/2002 |
|----|--------------|---------|
| JP | 2004534566 A | 11/2004 |
| WO | 02076549 A2 | 10/2002 |

* cited by examiner

AUTOMATIC EXTERNAL DEFIBRILLATOR FOR ADULT AND PEDIATRIC PATIENTS

CROSS-REFERENCE TO PRIOR APPLICATIONS

This application claims the benefit or priority of and describes relationships between the following applications: wherein this application is a continuation of U.S. patent application Ser. No. 11/721,549, now U.S. Pat. No. 9,079,044, filed Jun. 13, 2007, which is the National Stage of International Application No. PCT/IB2005/054249, filed Dec. 14, 2005, which claims the priority of U.S. Provisional Application 60/637,682, filed Dec. 20, 2004, all of which are incorporated herein in whole by reference.

This invention relates to automatic external defibrillators (AEDs) and, in particular, to AEDs which are operable for defibrillation of both adult and pediatric patients.

AEDs are conventionally designed to resuscitate adult patients with ventricular fibrillation (VF), as adults are the most likely to be afflicted with VF. However, a small percentage of juveniles are also susceptible to VF and can benefit from AED resuscitation. Since only a small percentage of patients are likely to be juveniles, the common approach in designing an AED for a pediatric patient is to modify a standard adult AED to be operable in a pediatric mode. An example of an AED which has a pediatric mode is found in U.S. Pat. No. 6,370,428. The most significant difference between the adult and pediatric modes is the amount of energy delivered by the AED defibrillation shock. Energy levels of approximately 150 Joules are used to defibrillate adult patients, whereas pediatric patients generally receive shocks of about 50 Joules. The lower energy pulses can be provided by resetting an energy selector switch so that the pulse delivered by the AED unit is at the lower energy level. In other embodiments such as those shown in U.S. Pat. Nos. 6,134,468 and 6,374,137, shocks are always delivered by the AED at the higher energy level but for pediatric patients an electrode pad set is used with attenuators in the lines which attenuate the energy delivered by the AED down to the lower pediatric level. Another difference between pediatric and adult modes is the ECG analysis employed, which needs to account for the differences in heart rhythms between adult and pediatric patients. Other differences are the CPR prompts employed, the location of electrode pad placement on a pediatric patient, and shock advisory algorithms.

As is well known, defibrillation must commence within a short time after the onset of VF in order for the patient to have any reasonable chance of survival. Studies have shown that under the stresses of this time pressure, responders, particularly layperson responders, often become confused by even simple procedures and devices. In particular, it has been shown that responders can find the resetting of AED controls and special electrodes for pediatric patients to be daunting tasks, especially when the patient is a young child. The presence of a special button on the AED for the pediatric mode is often overlooked in the intensity of a rescue. On the other hand, since the overwhelming percentage of patients are adults, the presence of a button or switch for pediatric patients is unnecessary and only adds to the confusion during an adult rescue. But making the pediatric control less obvious can obscure it for the times when it is needed. Accordingly it is desirable to enable the switching of an AED to the pediatric mode to be as simple as possible and without adding distraction during adult rescues so that even inexperienced personnel under significant stress can resuscitate a pediatric patient successfully.

In accordance with the principles of the present invention, an AED unit is described which can be switched to a pediatric rescue protocol upon insertion of a simple key-like device. The key-like device is separate from the AED and requires only insertion to change the mode of the AED. When inserted into the AED unit, a pediatric rescue protocol is executed by the AED, providing audible prompts for a pediatric patient, ECG analysis of a pediatric heartbeat, and reduced energy delivery. The protocol may optionally also provide CPR coaching for a pediatric patient.

In an illustrated embodiment the key-like device also changes the electrode pad placement illustration on the AED unit from adult pad placement to pediatric pad placement. The key-like device is inserted into an aperture which is hermetically sealed to prevent entry of dust or contaminants into the AED unit through the aperture. No special buttons or controls need to be set or reset to enter the pediatric mode; the changeover is completely automatic once the key-like device has been inserted into the AED unit.

Figure 1:
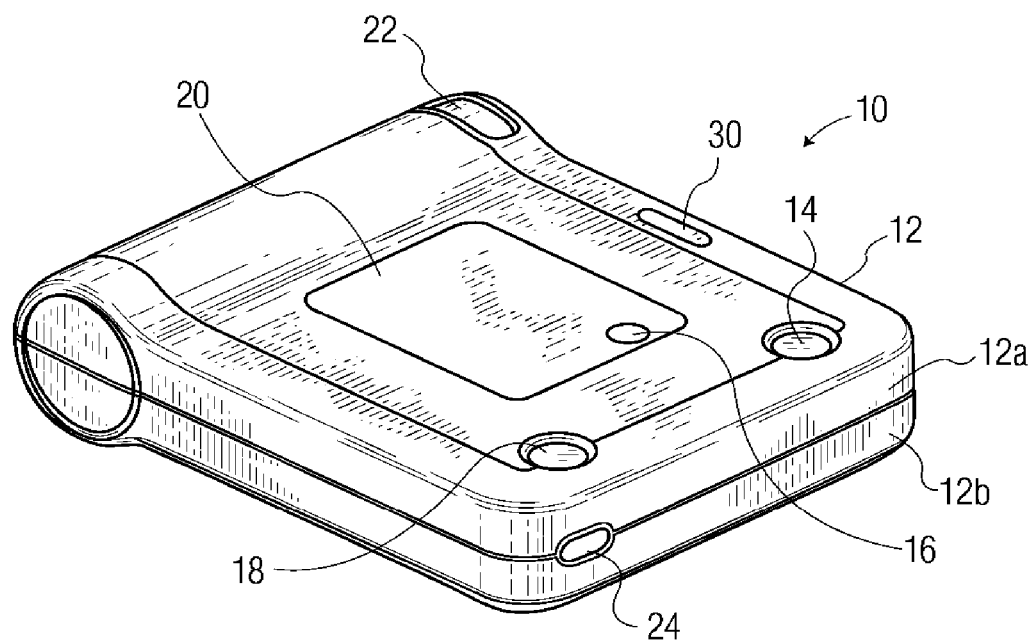
FIG. 1 is a perspective drawing of an AED unit constructed in accordance with the principles of the present invention.

Referring first to FIG. 1, an AED unit 10 is shown in perspective. An AED unit such as the one shown has dimensions of approximately 2.5 inches by 6 inches by 8 inches and weights about 4 pounds. The AED unit is enclosed in a case 12 having two halves 12a and 12b which are sealed together to prevent the ingress of water, dust and contaminants to the electronic modules inside the case. The AED unit 10 has an on/off button 14 and a shock button 18 which is depressed to deliver a defibrillating shock. The AED unit has an information button 16 which flashes when information concerning a protocol is available for the operator. The AED unit has a panel 20 which may be a display for the display of visual information and instructions for the operator. In the embodiment described below information and instructions are delivered audibly through a loudspeaker or headset and a visual display is not necessary. The AED unit has a connector 22 into which the mating connector of an electrode pad set is plugged. An infrared (IR) port 24 for data communication to and from the AED unit is located on the side of the case 12.

In accordance with the principles of the present invention the AED unit 10 has a slot 30 into which a key-like device (referred to herein as a "pedi-key") is inserted to switch the AED to a pediatric rescue protocol. The slot 30 does not provide an entry into the inside of the case 12. Instead, the walls of the interior of the slot are a continuation of the case material 12a, 12b so that the slot allows no physical entry into the interior of the case. Thus, dust, dirt and other contaminants will not enter the case through the slot 30 as the interior of the slot is completely sealed. To prevent dust and contaminants from accumulating in the slot, the aperture of the slot 30 extends completely through the bottom of the case 12*b*.

Figure 2:
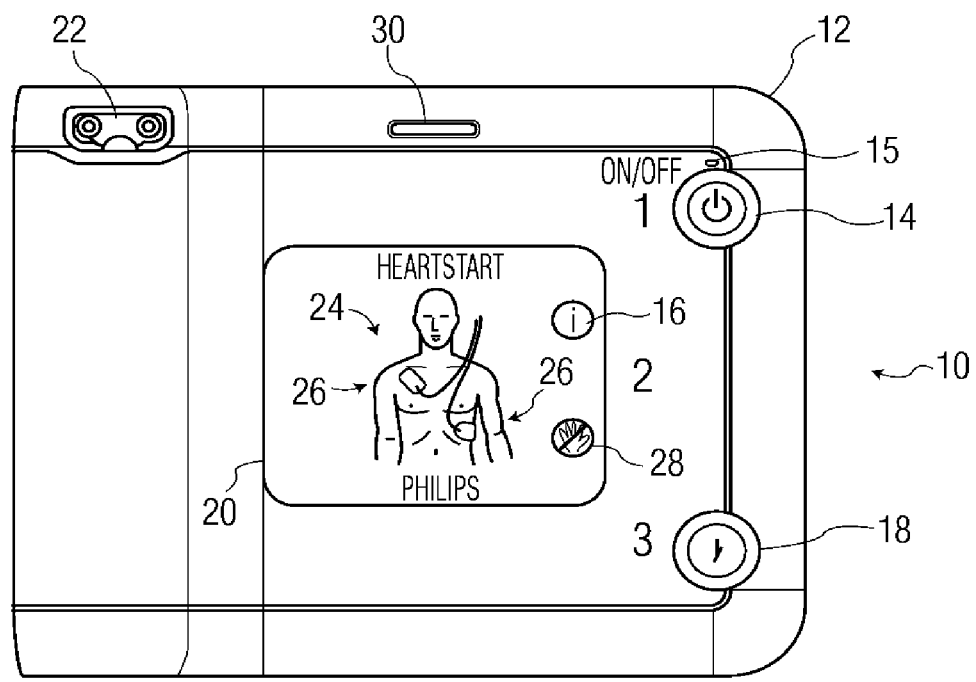
FIG. 2 is a top plan view of the case of the AED unit of FIG. 1.

FIG. 2 is a top plan view of the upper surface of the AED 10 in a constructed embodiment. The panel 20 is seen to contain a sketch 24 of the head and torso of a human with electrode pads (indicated by arrows 26) attached just below the right collarbone and over the lower left ribcage, the preferred electrode placement positions for an adult. Just behind the membrane covering panel 20 on which the sketch 24 is printed are two LEDs positioned at the indicated locations 26 of the two electrode pads. When the audible instructions of the protocol are instructing the rescuer to attach the electrode pads to the patient, the two LEDs at locations 26 flash on and off, drawing the attention of the rescuer to this indication of proper electrode pad placement.

Also located on the pad is a "Do Not Touch" indicator 28, drawn as a hand with a slash across it. An LED behind the drawing flashes on and off when the shock is about to be delivered to warn the rescuer and others to stand clear of and not touch the patient while the shock is being delivered. Above the on/off button 14 is a small green status LED 15, which blinks periodically while the AED unit is in its standby state to indicate that the AED unit is operating properly and ready for use.

Figure 3:
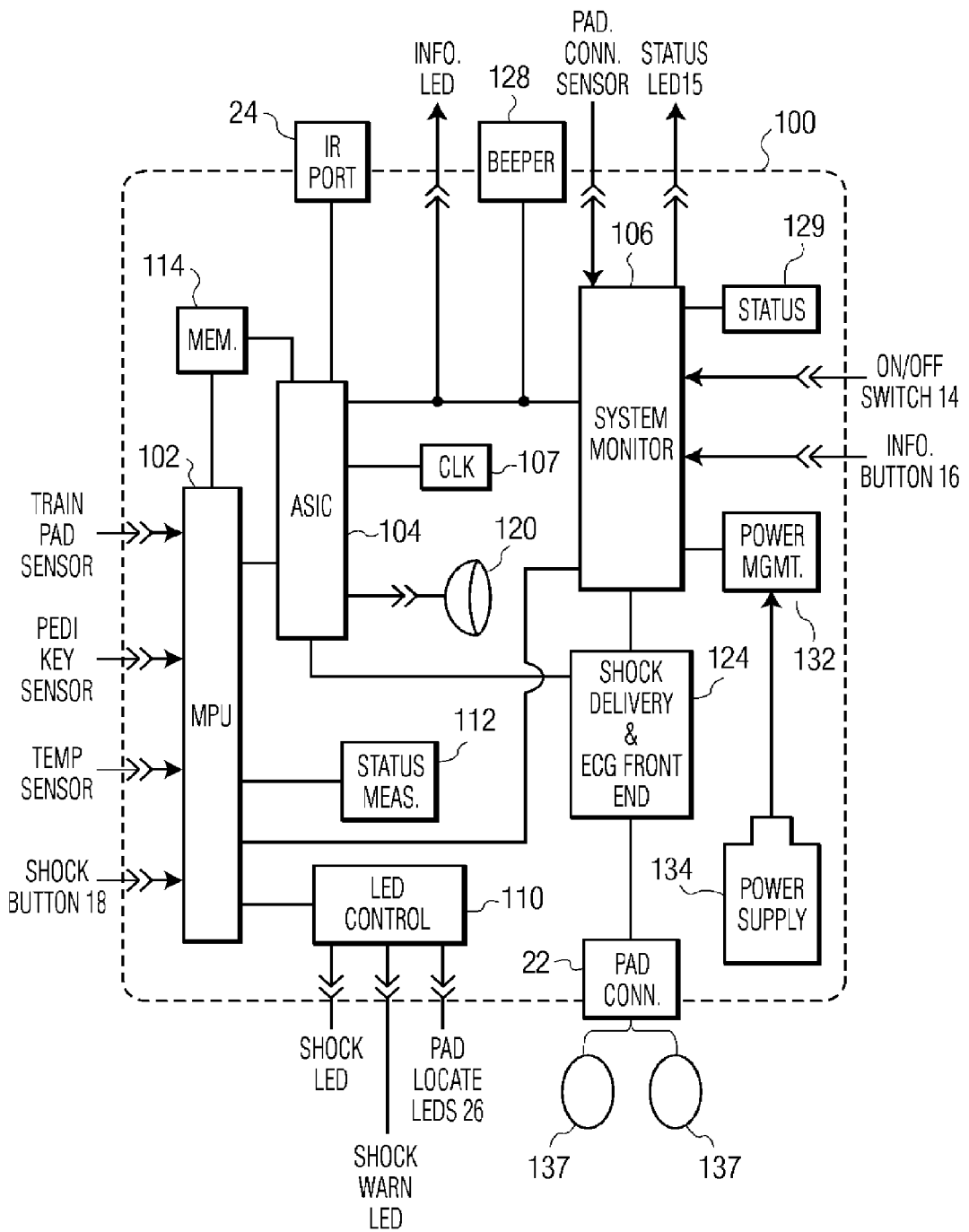
FIG. 3 illustrates in block diagram form the major components of an AED unit constructed in accordance with the principles of the present invention.

The major components of an AED are shown in FIG. 3 in block diagram form. Further detailed information about the operation of an AED can be obtained in U.S. Pat. No. 5,836,993, to Cole for "Electrotherapy Device Control System and Method," the specification of which is incorporated herein.

In this illustration, defibrillator control functions are divided among a microprocessor unit (MPU) 102, an application-specific integrated circuit (ASIC) 104 and a system monitor 106.

MPU 102 performs program steps according to software instructions provided to it from memory 114 which may comprise one or more of EPROM, RAM and flash ROM memory. MPU 102 controls the operation of certain system LEDs through an LED control circuit 110, including an LED associated with the shock button 18, the LED associated with the Do Not Touch indicator 28, and the LEDs which indicate the locations 26 of the electrode pads on the torso sketch 24. MPU 102 also receives system status information as shown by block 112, temperature information from the interior of the case 12 from a temperature sensor (not shown), and a signal from a sensor when training pads are plugged into the connector 22. The training pad sensor can be a magnetic sensor associated with connector 22 which senses the field of a small magnet integrated into the connector of a training electrode pad set.

In accordance with the principles of the present invention the MPU is also responsive to a signal from a pedi-key sensor associated with slot 30 when a pedi-key is inserted into a slot to switch the operation of the AED unit to a pediatric rescue protocol. The pedi-key sensor is preferably one which does not adversely affect the hermetic seal of the slot, such as a magnetic sensor (e.g., a reed switch inside the case) which responds to a small magnet in the pedi-key, or an optical sensor which optically detects (as by means of an LED and photocell) the presence of the pedi-key in the slot 30. The sensor could also be a pushbutton or switch which is activated by insertion of the pedi-key or electrical contacts which are electrically connected by an electrically conductive pedi-key.

ASIC 104 implements the memory map to system memory 114. ASIC 104 is clocked by a clock 107 and also controls a speaker 120 which delivers audible instructions during use of the AED. ASIC 104 can actuate a relay within the shock delivery and ECG front-end system 124 in response to actuation of the shock button 18 by a user during treatment. ASIC 104 will actuate an LED associated with the information button to signal to the user that information is available and can be accessed by depressing the information button 16. The ASIC also provides the interface to the IR port 24 through which new program information can be loaded into the AED unit and rescue data can be communicated to another data storage or analysis system.

System monitor 106 performs automatic self-tests of the AED and its components. The system monitor 106 controls the status LED 15 to indicate that the self-tests are showing proper system operation, and activates beeper 128 to provide an audible alert when the system is not operating properly. Details of suitable self-tests may be found in U.S. Pat. No. 5,879,374, to Powers, et al. for "External Defibrillator with Automated Self-Testing Prior to Use," the specification of which is incorporated herein by reference. System monitor 106 is also the defibrillator's interface with the on/off switch 14, the information button 16, and a sensor associated with connector 22 which signals the connection of a specific type of electrode pads 137 to the AED unit. System monitor 106 controls a power management subsystem 132 to provide power to operate system components from power supply 134 and to provide energy to the shock delivery system's capacitor(s) for a therapeutic shock during treatment. System monitor 106 also interfaces with the defibrillator's ECG front end, enables the shock delivery system to deliver a shock in response to detection of a patient ECG pattern requiring treatment (and actuation of the shock button 18), and controls delivery of the shock to electrode pad connector 22 in response to shock delivery status information (e.g., patient impedance) obtained during delivery of the shock. Further information regarding this last function may be found in U.S. Pat. No. 5,735,879 to Gliner et al. for "Electrotherapy Method for External Defibrillators," and U.S. Pat. No. 5,607,454, to Cameron et al. for "Electrotherapy Method and Apparatus," the specifications of which are incorporated herein.

As described previously, electrical connector 22 may communicate directly with the system monitor 106 to identify the electrode type, or electrical connector 22 may communicate with system monitor 106 via an identifier receiver that interfaces between the system monitor and the identifier of the electrical connector 22. For example, in an optical encoding embodiment, photodetectors could act as an identifier receiver in communication between the system monitor and the electrical connector 22.

These defibrillator components communicate with each other over suitable communication buses, as shown.

Figure 4:
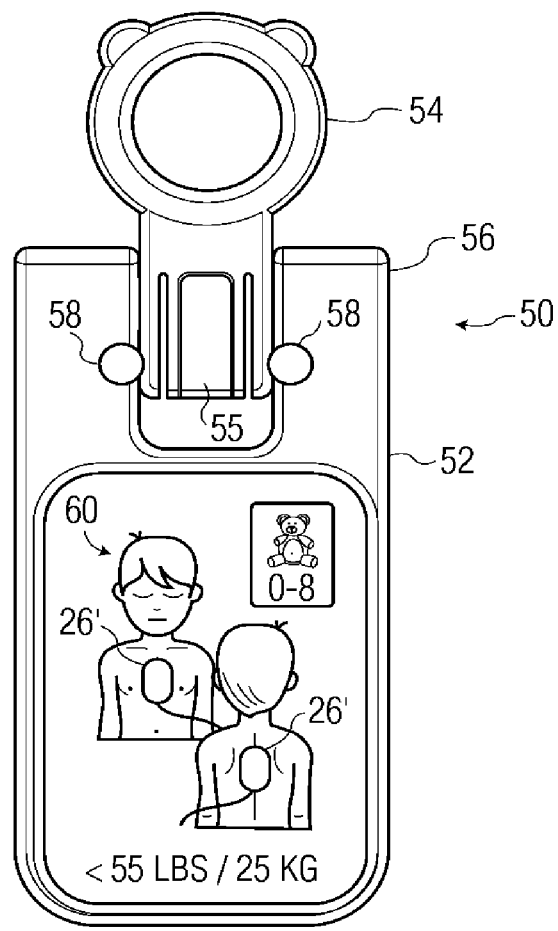
FIG. 4 is a plan view of a key-like device for switching an AED unit to the pediatric mode.

FIG. 4 illustrates one embodiment of a pedi-key 50 constructed in accordance with the principles of the present invention. In this embodiment the pedi-key 50 is constructed of two polymeric parts 52 and 54 which are pivotally interconnected by a shaft 56 extending through the top of the pad placement part 52 and the middle of the key part 54. The key part 54 is formed in a ring at the top so that the pedi-key can be tethered or tied to the AED unit 10 or its carrying case. Two stops 58 are molded in the pad placement part 52 which enable the key part 54 to pivot only in the direction which facilitates its use with the AED unit as discussed below. The distal end of the key part 54, which is inserted into the slot 30 during use of the pedi-key, is covered with a magnetic strip 55. When the slot 30 uses an optical sensor for the pedi-key, the distal end of the key part 54 is covered with a reflective strip 55.

In this embodiment the pad placement part 52 contains a pediatric sketch 60 showing the proper placement of the electrode pads of the AED unit on a pediatric patient. As the sketch 60 illustrates, the electrode pads are properly placed on the chest and back of a pediatric patient for treatment. The sketch 60 may have the pediatric pad positions 26' drawn on the sketch as shown. However, in a constructed embodiment the oval space inside the pad positions 26' comprises holes formed through the pad placement part 52.

Figure 5:
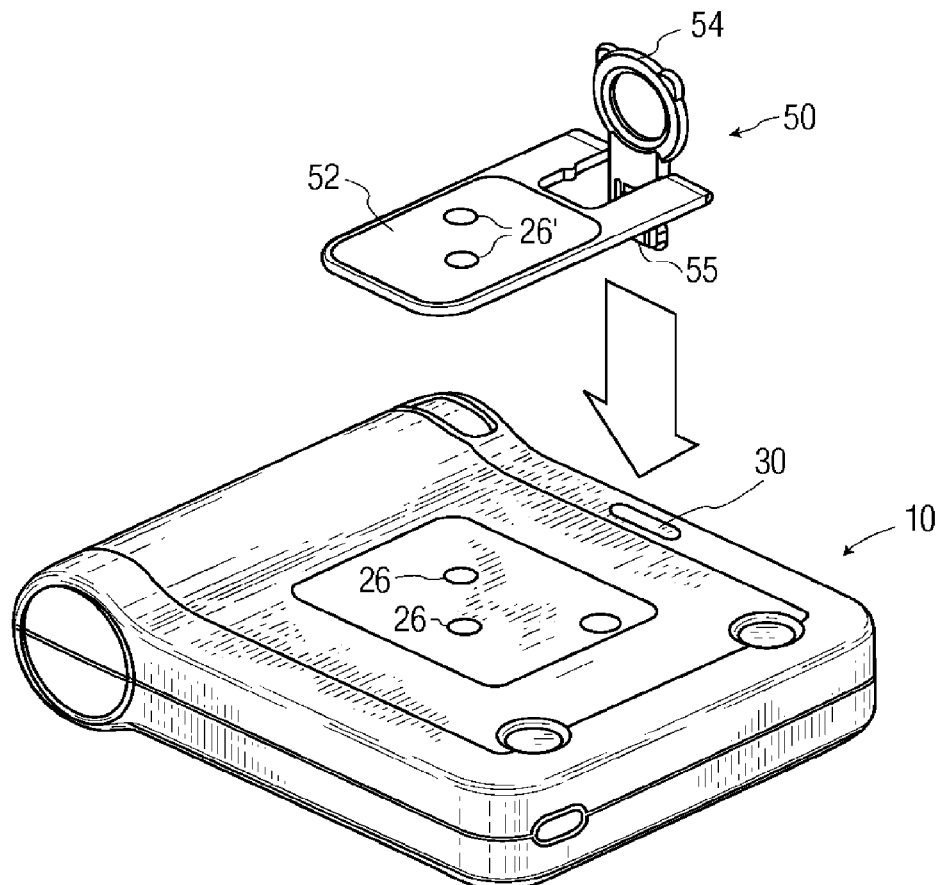
FIG. 5 illustrates the insertion of a pediatric mode key into an AED unit.
Figure 6:
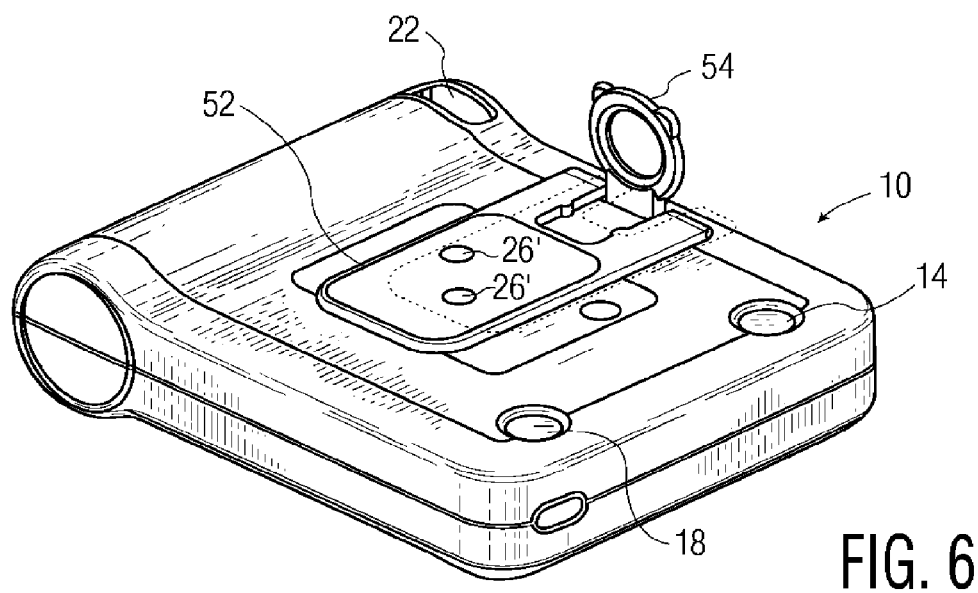
FIG. 6 illustrates the AED unit of FIG. 5 with the pediatric mode key inserted.

FIGS. 5 and 6 illustrate the insertion of the pedi-key 50 of FIG. 4 into the slot 30 of the AED unit 10. The key part 54 is pivoted to be perpendicular to the pad placement part 52 as shown in FIG. 5. The distal end 55 of the key part 54 is then inserted into the slot 30 as indicated by the large arrow in the drawing. When the key part 54 is inserted, the holes of the pediatric pad positions 26' of the pediatric sketch 60 are in alignment with the LEDs 26 of the adult sketch 24. The pad placement part 52 will then completely cover the adult sketch 24 so that the rescuer will only see the pediatric sketch 60. Moreover, the holes through the pediatric pad positions 26' of the pediatric sketch 60 will allow the light of the AED unit LEDs 26 to be visible through the pad positions 26' of the pediatric sketch.

In use, when a pediatric patient is to receive treatment, the pedi-key is inserted in the AED unit 10 as shown in FIG. 6 and the AED unit 10 is turned on by depressing the on/off button 14. The sensor associated with the slot 30 will immediately sense the presence of the pediatric key and the MPU 102 will cause the AED unit to immediately begin executing a pediatric rescue protocol instead of an adult protocol. Alternatively, insertion of the pedi-key into the AED unit 10 can cause the AED unit to turn on as described in U.S. Pat. No. 6,556,864 to Picardo et al. entitled "Object Activated Defibrillator" and to begin execution of a pediatric protocol in accordance with the present invention. The audible instructions will begin by instructing the rescuer to open and prepare the electrode pads for attachment to the patient. When the pad connector is plugged into the AED unit connector 22 and the pads are ready to be applied, the LEDs 26 on the base unit will begin to flash, drawing the attention of the rescuer to the pediatric sketch 60 on the pedi-key 52 and the flashing pediatric pad locations 26'. When the pads are successfully attached the pediatric protocol will begin analysis of a pediatric ECG waveform and determine whether a shock is appropriate. If it is, the rescuer will be warned not to touch the patient and the shock button 18 will flash to alert the rescuer to press the button to deliver the shock. Shock energy appropriate for a pediatric patient, e.g., 50 Joules, is then delivered to the patient.

If desired the protocol can also include instructions for administering CPR to a pediatric patient.

In the foregoing embodiment it is seen that insertion of the pedi-key 50 is all that is required to change the functioning of the AED unit 10 to that of a pediatric AED. No setting of switches or other settings or controls are required. There is thus no ambiguity or possibility for a rescuer to incorrectly set the AED for a pediatric rescue. Furthermore, by providing a separate article rather than a control on the AED unit, compliance with regulatory approvals are facilitated. For instance, some AEDs are now approved for use with adult patients without a physician's prescription. However, over-the-counter use with pediatric patients may still require a physician's prescription. An over-the-counter AED constructed in accordance with the principles of the present invention will readily function for adult rescues without the pedi-key but not for non-prescribed pediatric rescues. The pedi-key can then be made the prescription device and, when properly prescribed and obtained, can be used to convert the operation of the adult AED unit into a prescription pediatric unit.

The use of an insertable device to change the AED to the pediatric mode can afford several other advantages. As compared with the prior art approach of an electrode pad set with an in-line attenuator, the same electrode pad set can be used for both pediatric patients or adults. There is no need to store or attach a special pad set for a pediatric patient. Moreover, when the single pad set is attached to the AED during storage of the unit, the pad set can be tested regularly to assure that it has not deteriorated from desiccation. A separately stored pad set cannot be tested, nor can its special pediatric attenuator; it may be years before such a pad set is needed, during which time deterioration may have adversely affected its effectiveness. In an embodiment of the present invention, the sensor inside the AED unit adjacent the slot 30 can be routinely automatically tested along with the other AED components. An embodiment of the present invention can thus assure the readiness of an AED for a pediatric patient through periodic automatic testing and can alert potential users to problems due to aging before the AED is needed for emergency use.

Other embodiments in accordance with the principles of the present invention will also readily occur to those skilled in the art. For instance, if the AED unit is operable with one type of electrode pads for adult rescues and a different type of electrode pads for pediatric rescues, the connector of the pediatric electrode pad set can also comprise the pedi-key which, when plugged into the AED unit to connect the pads to the AED unit, is sensed to cause the AED unit to execute the pediatric rescue protocol.

What is claimed is:

1. An AED system for use with either adult or pediatric patients comprising:
   an electrode pad having a mating connector;
   a pedi-key that comprises a key part moveably coupled with a pad placement part, the key part having a distal end and the pad placement part having an indicator of a placement of the electrode pad on a pediatric patient; and
   an AED unit including
   a casing having a surface with an indication of electrode pad placement for an adult patient,
   an aperture disposed at a first location on the AED unit casing and shaped to receive the pedi-key key part distal end,
   an electrode pad connector disposed at a second location on the AED unit casing and shaped to receive the mating connector, and
   circuitry internal to the casing for delivering a defibrillating shock and for being selectively operable to switch from an adult rescue protocol to a pediatric rescue protocol responsive to a sensed receiving of the pedi-key key part distal end within the aperture, further wherein the pedi-key pad placement part overlies the indication of electrode pad placement for the adult patient in response to the pedi-key part distal end being received within the aperture, and wherein the AED system is disposed such that the pedi-key and the electrode pad connector may concurrently be received in the respective aperture and mating connector.

2. The AED system of claim 1, wherein the aperture is hermetically sealed off from the interior of the AED unit.

3. The AED system of claim 2, wherein the AED unit further includes a sensor located proximate the aperture for sensing a presence of the pedi-key key part distal end in the aperture.

4. The AED system of claim 3, wherein the pedi-key key part distal end comprises a magnetic strip and the sensor comprises a magnetic sensor.

5. The AED system of claim 3, wherein the pedi-key key part distal end comprises a reflective strip and the sensor comprises an optical sensor.

6. The AED system of claim 3, wherein the circuitry further comprises a testing circuit operable to automatically test the sensor.

7. The AED system of claim 1, wherein the pediatric rescue protocol includes placing an electrode pad on a pediatric patient and delivering a defibrillating shock at a level appropriate for a pediatric patient.

8. The AED system of claim 7, wherein the pediatric rescue protocol further includes analyzing a pediatric ECG signal.

9. The AED system of claim 7, wherein the pediatric rescue protocol further includes audible instructions for defibrillating a pediatric patient.

10. The AED system of claim 1, further comprising a tether disposed between the pedi-key and one of the AED unit or an AED unit carrying case.

11. The AED system of claim 1, wherein the electrode pad connector and the mating connector of the electrode pad are stored in a received disposition prior to AED system activation, and wherein the circuitry further comprises a system monitor operable to assure that the electrode pad has not deteriorated from desiccation.

12. A method for selectively operating an AED unit which is operable by execution of an adult rescue protocol or a pediatric rescue protocol as a pediatric AED system comprising the steps of:
    connecting an electrode pad mating connector to a mating connector disposed on a casing of the AED unit, the casing having a surface with an indication of electrode pad placement for an adult patient;
    subsequent to the connecting step, inserting a separate device into an aperture disposed on the AED unit casing, wherein the separate device comprises a key part moveably coupled with a pad placement part, the key part having a distal end and the pad placement part having an indicator of a placement of the electrode pad on a pediatric patient;
    sensing the insertion of the separate device into the aperture disposed on the AED unit, wherein the separate device pad placement part is caused to overlie the indication of electrode pad placement for the adult patient in response to the separate device key part distal end being received within the aperture; and
    executing the pediatric rescue protocol responsive to the sensing step.

13. The method of claim 12, wherein the separate device comprises a pedi-key, and
    wherein the sensing step comprises sensing the presence of the pedi-key in the aperture.

14. The method of claim 12, wherein executing the pediatric rescue protocol includes:
    directing the attachment of an electrode pad to a pediatric patient; and
    applying a shock energy appropriate for a pediatric patient.

15. The method of claim 14, wherein executing the pediatric rescue protocol further includes analyzing a pediatric ECG signal.

16. The method of claim 14, wherein directing the attachment of an electrode pad comprises audibly instructing a rescuer in the attachment of an electrode pad to a pediatric patient.

17. The method of claim 14, wherein executing the pediatric rescue protocol further includes providing CPR instructions for a pediatric patient.

18. The method of claim 12, wherein executing the pediatric rescue protocol further comprises providing visual instructions for applying an electrode pad to a pediatric patient.

19. The method of claim 12, further comprising a step of activating the AED unit for use after the connecting step.

20. The method of claim 19, further comprising a step of automatically testing one of the electrode pad or a sensor in the AED unit for sensing the insertion of the separate device prior to the activating step.

\* \* \* \* \*